United States Patent [19]

Au-Young et al.

[11] Patent Number: 6,043,222

[45] Date of Patent: Mar. 28, 2000

[54] TWO NEW HUMAN DNAJ-LIKE PROTEINS

[75] Inventors: Janice Au-Young, Berkeley; Preeti Lal, Sunnyvale; Olga Bandman, Mountain View, all of Calif.

[73] Assignee: Incyte Pharmaceuticals, Inc., Palo Alto, Calif.

[21] Appl. No.: 09/388,993

[22] Filed: Sep. 2, 1999

Related U.S. Application Data

[62] Division of application No. 09/235,373, Jan. 20, 1999, which is a division of application No. 08/868,288, Jun. 3, 1997, Pat. No. 5,922,567.

[51] Int. Cl.⁷ .......................... A61K 38/00; A01N 37/18; C07K 1/00
[52] U.S. Cl. ................ 514/12; 514/2; 530/350; 530/827; 530/839
[58] Field of Search .......................... 514/2, 12; 530/350, 530/827, 839

[56] References Cited

PUBLICATIONS

Hightower, L.E., "Heat Shock, Stress Proteins, Chaperones, and Proteotoxicity", *Cell*, 66: 191–197 (1991).

Udono, H., et al., "Comparison of Tumor–Specific Immunogenicities of Stress–Induced Proteins gp96, hsp90, and hsp70¹", *Journal of Immunology*, 152: 5398–5403 (1994).

Fang, Y., et al., "Hsp90 Regulates Androgen Receptor Hormone Binding Affinity in Vivo", *The Journal of Biological Chemistry*, 271 (45) : 28697–28702 (1996).

Young, R.A., "Stress Proteins and Immunology", *Annu. Rev. Immunol.* 8: 401–20 (1990).

Marber, M.S., et al., "Overexpression of the Rat Inducible 70–kD Heat Stress Protein in a Transgenic Mouse Increases the Resistance of the Heart to Ischemic Injury", *J. Clin. Invest.*, 95: 1446–1456 (1995).

Simon, M.M., et al., "Heat Shock Protein 70 Overexpression Affects the Response to Ultraviolet Light in Murine Fibroblasts", *J. Clin. Invest.*, 95: 926–933 (1995).

Sargent, C.A., et al., "Human major histocompatibility complex contains genes for the major heat shock protein HSP70", *Proc. Natl. Acad. Sci. USA*, 86: 1968–1972 (1989).

Hendrick, J.P., et al., "Control of folding and membrane translocation by binding of the chaperone DnaJ to nascent polypeptides", *Proc. Natl. Acad. Sci. USA*, 90: 10216–10220 (1993).

Dix, D.J., et al., "Targeted gene disruption of Hsp70–2 results in failed meiosis, germ cell apoptosis, and male infertility", *Proc. Natl. Acad. Sci. USA*, 93: 3264–3268 (1996).

Ohtsuka, K., "Cloning of a cDNA for Heat–Shock Protein hsp40, A Human Homologue of Bacterial DnaJ", *Biochemical and Biophysical Research Communications*, 197: 235–240 (1993).

Cheetham, M.E., et al., "Human homolgues of the bacterial heat–shock protein DnaJ are Preferentially expressed in neurons", *Biochem. J.*, 284: 469–476 (1992).

Chellaiah, A., et al., (GI 306714) GenBank Sequence Database (Accession L08069), National Center for Biotechnology Information: National Library of Medicine, Bethesda, Maryland 20849.

Chellaiah, A., et al., (GI 306713) GenBank Sequence Database (Accession L08069), National Center for Biotechnology Information: National Library of Medicine, Bethesda, Maryland 20849.

Cheetham, M.E., (GI 32469) GenBank Sequence Database (Accession X63368), National Center for Biotechnology Information: National Library of Medicine, Bethesda, Maryland 20849.

Cheetham, M.E., (GI 32470) GenBank Sequence Database (Accession X63368), National Center for Biotechnology Information: National Library of Medicine, Bethesda, Maryland 20849.

Cheetham, M.E., (GI 32468) GenBank Sequence Database (Accession X63368), National Center for Biotechnology Information: National Library of Medicine, Bethesda, Maryland 20849.

Brightman, S. et al. "Isolation of a mouse cDNA encoding MTJ1, a new murine member of the DnaJ family of proteins," *Gene* 153:249–254 (1995).

Strausberg, R. "NCI–Cancer Genome Anatomy Project," EMBL Database entry Hs1187407; Acc No. AA282838 (Apr. 5, 1997).

Hillier, et al. "The WashU–Merck EST project," EMBL Database entry Hs505366; Acc No. W67505 (Jun. 16, 1996).

Hillier, et al. "The WashU–Merck EST project," EMBL Database entry Hs314359; Acc No. W65314 (1994).

*Primary Examiner*—Rebecca E. Prouty
*Assistant Examiner*—Elizabeth Slobodyansky
*Attorney, Agent, or Firm*—Colett C. Muenzen; Incyte Pharmaceuticals, Inc.

[57] ABSTRACT

The invention provides a two new human DnaJ-like proteins (HSPJ1 or HSPJ2) and polynucleotides which identify and encode HSPJ1 or HSPJ2. The invention also provides expression vectors, host cells, agonists, antibodies and antagonists. The invention also provides methods for treating disorders associated with expression of HSPJ1 or HSPJ2.

2 Claims, 12 Drawing Sheets

```
5' TCT CAC CGG GAC TCG GGA CTC CCG GGA AGT GGA CCG GCA GAA GAG GGG GCT AGC
      9         18          27          36          45          54

TAG CTG TCT CTG CGG GAG ACC CCC GCG CCC CCC CGG TGT GAG GCG GCC
     63          72          81          90          99         108

TCA CAG GGC CGG GTG GGC TGG CGA GCC GAC GCG GCG GCG GAG GCT GTG AGG
    117         126         135         144         153         162

AGT GTG TGG AAC AGG ACC CGG GAC AGA GGA ACC ATG GCT CCG CAG AAC CTG AGC
    171         180         189         198         207         216
                                         M   A   P   Q   N   L   S

ACC TTT TGC CTG CTG TTG CTA TAC CTC ATC GGG GCG GTG ATT GCC GGA CGA GAT
    225         234         243         252         261         270
     T   F   C   L   L   L   Y   L   I   G   A   V   I   A   G   R   D

TTC TAT AAG ATC TTG GGG GTG CCT CGA AGT GCC TCT ATA AAG GAT ATT AAA AAG
    279         288         297         306         315         324
     F   Y   K   I   L   G   V   P   R   S   A   S   I   K   D   I   K   K

GCC TAT AGG AAA CTA GCC CTG CAG CTT CAT CCC GAC CGG AAC CCT GAT GAT CCA
    333         342         351         360         369         378
     A   Y   R   K   L   A   L   Q   L   H   P   D   R   N   P   D   D   P

FIGURE 1A
```

```
        387          396          405          414          423          432
CAA GCC CAG GAG AAA TTC CAG GAT CTG GGT GCT TAT GAG GTT CTG TCA GAT
 Q   A   Q   E   K   F   Q   D   L   G   A   Y   E   V   L   S   D 441          450          459          468          477          486
AGT GAG AAA CGG AAA CAG TAC GAT ACT TAT GGT GAA GAA GGA TTA AAA GAT GGT
 S   E   K   R   K   Q   Y   D   T   Y   G   E   E   G   L   K   D   G 495          504          513          522          531          540
CAT CAG AGC TCC CAT CAG GGA GAC ATT TTT TCA CAC TTC TTT GGG GAT TTT GGT TTC
 H   Q   S   S   H   Q   G   D   I   F   S   H   F   F   G   D   F   G   F 549          558          567          576          585          594
ATG TTT GGA GGA ACC CCT CGT CAG CAA GAC AGA ATT CCA AGA GGA AGT GAT
 M   F   G   G   T   P   R   Q   Q   D   R   N   I   P   R   G   S   D 603          612          621          630          639          648
ATT GTA GAT CTA GAA GTC ACT TTG GAA GAA GTA TAT GCA GGA AAT TTT GTG
 I   I   V   D   L   E   V   T   L   E   E   V   Y   A   G   N   F   V 657          666          675          684          693          702
GAA GTT AGA AAC AAA CCT GTG GCA AGG CAG GCT CCT GGC AAA CGG AAG TGC
 E   V   R   N   K   P   V   A   R   Q   A   P   G   K   R   K   C 711          720          729          738          747          756
AAT TGT CGG CAA GAG ATG CGG ACC ACC CAG CTG GGC CCT GGG CGC TTC CAA ATG
 N   C   R   Q   E   M   R   T   T   Q   L   G   P   G   R   F   Q   M
```

FIGURE 1B

```
     765         774         783         792         801         810
ACC CAG GAG GTG GTC TGC GAC GAA CCT AAT GTC AAA CTA GTG AAT GAA GAA
 T   Q   E   V   V   C   D   E   P   N   V   K   L   V   N   E   E 819         828         837         846         855         864
CGA ACG CTG GAA GTA GAA ATA GAG CCT GGG GTG AGA GAC GGC ATG GAG TAC CCC
 R   T   L   E   V   E   I   E   P   G   V   R   D   G   M   E   Y,  P 873         882         891         900         909         918
TTT ATT GGA GAA GGT GAG CCT CAC GTG GAT GGG GAG CCT GGA GAT TTA CGG TTC
 F   I   G   E   G   E   P   H   V   D   G   E   P   G   D   L   R   F 927         936         945         954         963         972
CGA ATC AAA GTT GTC AAG CAC CCA ATA TTT GAA AGG AGA GGA GAT GAT TTG TAC
 R   I   K   V   V   K   H   P   I   F   E   R   R   G   D   D   L   Y 981         990         999        1008        1017        1026
ACA AAT GTG ACA GTC TCA TTA GTT GAG TCA CTG GTT GGC TTT GAG ATG GAT ATT
 T   N   V   T   V   S   L   V   E   S   L   V   G   F   E   M   D   I 1035        1044        1053        1062        1071        1080
ACT CAC TTG GAT GGT CAC AAG GTA CAT ATT TCC CGG GAT AAG ATC ACC AGG CCA
 T   H   L   D   G   H   K   V   H   I   S   R   D   K   I   T   R   P 1089        1098        1107        1116        1125        1134
GGA GCG AAN TAN TGG AAG AAA GGG GAA GGG CTC CCC AAC TTT GAC AAC AAC AAT
 G   A   X   X   W   K   K   G   E   G   L   P   N   F   D   N   N   N
```

FIGURE 1C

```
          1143       1152           1161           1170           1179           1188
ATC AAG GGC TCT TTG ATA ATC ACT TTT GAT GTG GAT TTT CCA AAA GAA CAG TTA
 I   K   G   S   L   I   I   T   F   D   V   D   F   P   K   E   Q   L 1197       1206           1215           1224           1233           1242
ACA GAG GAA GCG AGA GAA GGT ATC AAA CAG CTA CTG AAA CAA GGG TCA GTG CAG
 T   E   E   A   R   E   G   I   K   Q   L   L   K   Q   G   S   V   Q 1251       1260           1269           1278           1287           1296
AAG GTA TAC AAT GGA CTG CAA GGA TAT TGA GAG TGA ATA AAA TTG GAC TTT GTT
 K   V   Y   N   G   L   Q   G   Y 1305       1314           1323           1332           1341           1350
TAA AAT AAG TGA ATA AGC GAT ATT TAT TAT CTG CAA GGT TTT TTT GTG TGT GTT 1359       1368
TTT GTT TTT ATT TTC AAT ATG CAA GT 3'
```

```
254 RGDDLYTNVTSLVESLVGFEMDITHLDGHKVHISRD--K  136466
254 RGEDLFMCMDIQLVEALCGFQKPISTLDNRTIVITSHPGQ  GI 306714

292 ITRPGAXXWKKGEGLPNFDNNIKGSLIITFDVDFPKEQL   136466
294 IVKHGDIKCVLNEGMPIYRRPYEKGRLIEFKVNFPENGF   GI 306714

332 TEEAREGI------KQLLKQGSVQKV-----          136466
334 LSPDKLSLLEKLLPERKEVEETDEMDQVELVDFDPNQERR GI 306714

352 --YNGLQGY EDDEHHPRGGVQCQTS                136466
374 RHYNG-EAY                                 GI 306714
```

FIGURE 2B

```
                                                  9               18              27              36              45              54
5' CGN AGG AGA GNA AAG GAA AGN CGC CGC AGG AGC CGC CGC NAC CAC CAG CGN CAC 63              72              81              90              99             108
   ANT CCT GGN GCT NTG AGG AGA TTC GGG CCG TCA CCC TGC CTC CCC TGC TTC CCG 117             126             135             144             153             162
   CCA CCG GCC GCT TCT TTC CTC GGA CCC ATT CCA ACA ATC TCG TAA AAC ATG GTG
                                                                             M   V 171             180             189             198             207             216
   GAT TAC GAA GTT CTA GGC GTG CAG AGA CAT GCC TCA CCC GAG GAT ATT AAA
    D   Y   E   V   L   G   V   Q   R   H   A   S   P   E   D   I   K 225             234             243             252             261             270
   AAG GCA TAT CGG AAA CTG GCA GAG AAA TTC AAG TGG CAT CCA GAT AAA AAT CCT GAG AAT
    K   A   Y   R   K   L   A   E   K   F   K   W   H   P   D   K   N   P   E   N 279             288             297             306             315             324
   AAA GAA GCA GAG AGA AAA CAA GTA GCG GAG GCA TAT GAA GTG CTG
    K   E   A   E   R   K   Q   V   A   E   A   Y   E   V   L 333             342             351             360             369             378
   TCG GAT GCT AAG AAA CGG GAC ATC TAT GAC AAA TAT GGC AAA GAA GGA TTA AAT
    S   D   A   K   K   R   D   I   Y   D   K   Y   G   K   E   G   L   N

FIGURE 3A
```

```
387 GGT GGN GGN 396 GGT AGT CAT 405 TTT GAC AGT 414 CCA TTT GAA 423 TTT GGC TTC 432 ACA
     G   G   G       G   S   H       F   D   S       P   F   E       F   G   F       T
441 TTC CGT AAC 450 CCA GAT GTC 459 TTC AGG GAA 468 TTT TTT GGT 477 GGA AGG GAC 486 CCA TTT
     F   R   N       P   D   V       F   R   E       F   F   G       G   R   D       P   F
495 TCA TTT GAC 504 GAA GAC CCT 513 TTT GAG GAC 522 TTC TTT GGG 531 AAT CGA AGG 540 GGT
     S   F   D       E   D   P       F   E   D       F   F   G       N   R   R       G
549 CCC CGA GGA 558 AGC AGA CGA 567 GGG ACG GGG 576 TTT TTC TCT 585 GCG TTC AGT 594 GGA
     P   R   G       S   R   G       G   T   G       F   F   S       A   F   S       G
603 TTT CCG TCT 612 TTT GGA AGT 621 TCT TTT GAT 630 ACA GGA TTT 639 ACT TCA TTT 648
     F   P   S       F   G   S       S   F   D       T   G   F       T   S   F
657 GGG TCA CTA 666 GGT CAC GGG 675 GCC CTC ACT 684 TCA TTC TCT 693 TCC ACG TCA 702 TTT GGT
     G   S   L       G   H   G       G   L   T       S   F   S       S   T   S       F   G
711 AGT GGC ATG 720 GGC AAC TTC 729 AAA TCG ATA 738 TCA ACT TCA 747 ACT AAA ATG 756 GTT AAT GGC
     S   G   M       G   N   F       K   S   I       S   T   S       T   K   M       V   N   G
```

FIGURE 3B

```
                765         774         783         792         801         810
AGA AAA ATC ACT ACA AAG AGA ATT GTC GAG AAC GGT CAA GAA AGA GTA GAA GTT
 R   K   I   T   T   K   R   I   V   E   N   G   Q   E   R   V   E   V 819         828         837         846         855         864
GAA GAA GAT GGC CAG TTA AAG TCC TTA ACA ATA AAT GGT GTK GCC GAC GAC GAT
 E   E   D   G   Q   L   K   S   L   T   I   N   G   V   A   D   D,  D 873         882         891         900         909         918
GCC CTC GST GAG GAG CGC ATG CGG AGA GGC CAG AAC GTC CTG CCA GCC CAG CCT
 A   L   X   E   E   R   M   R   R   G   Q   N   V   L   P   A   Q   P 927         936         945         954         963         972
GCC GGC CTC CGA CCG AAG CCG CCC CGG CCT GCC TCG TTG CTG AGA CAC GNG
 A   G   L   R   P   K   P   P   R   P   A   S   L   L   R   H   X 981         990         999         1008        1017        1026
CCT CAT TGT CTC TCT AAG GAG GAG GGC GAG CAG GAG GAC CGA CCT TGG GCA CCC GNG
 P   H   C   L   S   K   E   E   G   E   Q   E   D   R   P   W   A   P   X 1035        1044        1053        1062        1071        1080
NCC TGG NNC CCC CTC GCT TCC NCA GCA GGN TTN NAA GAA GGT NGC AAG AGG ATG
 X   W   X   P   L   A   S   X   A   G   X   X   E   G   X   K   R   M 1089        1098        1107        1116        1125        1134
NAA GCA GAA GCA GAG AGA GGA GTC GAA GAA GTC GAC GAA GAA GTC GAC CAA TCA
 X   A   E   A   E   R   G   V   E   E   V   D   E   E   V   D   Q   S
```

FIGURE 3C

```
        1143           1152           1161           1170           1179           1188
CTA GAC CGG ACT TGA GGC ACG CGG TGC ACC CCC AGA CGC TGG CGC TCC ACC GTG
 L   D   R   T 1197           1206           1215           1224           1233           1242
CTC GGC ATG CGG TCG TGC ACA CGC GCT AGG TAG CAG CGT CGG TCA GGA CTG TCT 1251           1260           1269           1278           1287           1296
CGA GGC CAC ACT CGC TCG GCA GGA TTA TGC GAT CAC GGA TCA GTC AGA GCA GGG 1305           1314           1323
TCA GGA GAC GGG GCT GAC GGC ACG GGT GGC GGG G 3'
```

```
235 DDAL XEE RMRRGQNV -LPAQPAGLRPPKPPPRPAASLLRH XP  260873
211 DLARGLELSRREQQPSVTSRSGGTQVQQTPASCPLDSDLS    GI 32469
211 DLARGLELSRREQQPSVTSRSGGTQVQQTPASCPLDSDLS    GI 32470

274  H- - - - -CLSKEEGEQDRP- - - - - - - - - - - - - - -  260873
251 EDEDLQLAMAYSLSEMEAAGKKPAGGREAQHRRQGRPRPS    GI 32469
251 EDEDLQLAMAYSLSEMEAAGKKPAD- - - - - - - - - -    GI 32470

287 - - -WAP XX XPLAS XAGX XEG XKRM XAEAERGVEEEV    260873
291 TKIQAWGGPRRVRGVKQPNAVHPQRRRPLAASSEHRAQP     GI 32469
276 - - - - - - - - - - - - - - - - - - - - - - - - - - -    GI 32470

322 DQRQSL- - -DRT                                260873
331 DLIQILTGGSDSLWEEKRGVS                        GI 32469
276 - - - - - - - - - - -VF                       GI 32470
```

FIGURE 4B

TWO NEW HUMAN DNAJ-LIKE PROTEINS

This application is a divisional application of U.S. application Ser. No. 09/235,373, filed Jan. 20, 1999, which is a divisional of U.S. application Ser. No. 08/868,288, filed Jun. 3, 1997, issued Jul. 13, 1999, as U.S. Pat. No. 5,922,567.

FIELD OF THE INVENTION

This invention relates to nucleic acid and amino acid sequences of two new human DnaJ-like proteins and to the use of these sequences in the diagnosis, prevention, and treatment of cancer and inflammatory and immune disorders.

BACKGROUND OF THE INVENTION

Induction of heat shock proteins (Hsps), a class of molecular chaperones, is a physiological and biochemical response to abrupt increases in temperature or exposure to a variety of other metabolic insults including heavy metals, amino acid analogs, toxins, and to oxidative stress. This response occurs in all prokaryotic and eukaryotic cells and is characterized by repression of normal protein synthesis and initiation of transcription of Hsp-encoding genes. Under normal or nonstressed conditions, constitutively expressed Hsps facilitate proper protein folding and maturation, promote protein translocation across membranes, and regulate hormone receptor and protein kinase activity (Hightower, L. E., et al. (1991) Cell, 66: 191–197).

During cellular stress, Hsps form a complex with proteins that misfold or unfold, either "rescuing" these proteins from irreversible damage or increasing their susceptibility to proteolytic attack. Overexpression of Hsps in transgenic mice and rats, or prior heat treatment of normal animals to induce Hsps, protects the heart muscle from ischemic injury. Both heat shock-induced and exogenous Hsps protect smooth muscle cells from serum deprivation-induced cell death. Overexpression of Hsps also protects murine fibroblasts from both UV light injury and proinflammatory cytokines released during UV exposure. Specific Hsps bind immunosuppressive drugs and may play a role in modulation of immune responses. Hsps expressed in cancer cells can protect the cancer cells from the cytotoxic effects of drugs used in anticancer therapies. Hsps isolated from tumor cells, when purified and used as antigens, have been shown to provide immunity to the tumors from which they are isolated (Udono, H., et al. (1994) J. Immunol. 152: 5398–5403; Young R. A. (1990) Annu. Rev. Immunol. 8: 401–420; Marber, M. S., et al. (1995) J. Clin. Invest. 95: 1446–1456; Simon, M. M., et al. (1995) J. Clin. Invest. 95: 926–933).

Several of the constitutive Hsp genes are located in the major histocompatibility complex on chromosome 6, and members of the Hsp family play roles in T-cell mediated regulation of inflammation and immune recognition. Hsps bind to steroid hormone receptors, repress transcription in the absence of the ligand, and provide the proper folding of the ligand-binding domain in the presence of the hormone. Heat shock treatment of B-cells enhances processing of antigen and the assembly and function of MHC class II molecules (Sargent, C., A. et al (1989) Proc. Natl. Acad. Sci. 86: 1968–1972; Fang, Y., et al. (1996) J. Biol. Chem. 271: 28697–28702; Hendrick, J. P., et al (1993) Proc. Natl. Acad. Sci. 90: 10216–10220).

Knockout mice are providing additional information on the roles of Hsps. For example, female homozygous knockout mice for Hsp70 are found to undergo normal meiosis and are fertile. In contrast, the homozygous male knockout mice lack postmeiotic spermatids and mature sperm and are infertile (Dix, D. J. et al. (1996) Proc. Nat. Acad. Sci. 93: 3264–3268).

Hsps function in a variety of necessary cellular processes including protein translocation across membranes of cell organelles, nascent protein folding and multiunit protein assembly, antigen presentation, protein degradation in the lysosome, and uncoating of clathrin-coated vesicles. They are located in all major cellular compartments and function as monomers, multimers, or in complexes with other cellular proteins, which may determine the rate and specificity of the Hsp action. The yeast and bacterial homologues of the human Hsp70 function as a complex with the DnaJ gene product to accelerating the rate of ATP hydrolysis during protein folding and protein complex assembly. Human homologues of the DnaJ protein have recently been characterized and are found be strongly induced by heat shock and to have sequence similarity with the DnaJ protein family. The DnaJ homologue, hsp40, was shown to colocalize with hsp70 in the nuclei and nucleoli of heat-shocked HeLa cells. Two other homologues, HSJ1a and HSJ1b, are expressed primarily in the human hippocampus and frontal cortex (Ohtsuka, K. (1993) Biocem. Biophys. Res. Com. 197: 235–240 and Cheetham, M., E., et al. (1992) Biochem. J. 284: 469–476).

The discovery of two new DnaJ-like proteins and the polynucleotides encoding them satisfies a need in the art by providing new compositions which are useful in the diagnosis, prevention and treatment of cancer, inflammatory, and immune disorders.

SUMMARY OF THE INVENTION

The invention features two substantially purified polypeptides, new human DnaJ-like proteins (HSPJ1 and HSPJ2), having the amino acid sequence shown in SEQ ID NO:1, (HSPJ1), and SEQ ID NO:3, (HSPJ2), or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO.2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding HSPJ1 under conditions suitable for the expression of the polypeptide; and b) recovering the polypeptide from the host cell culture.

The invention also provides a pharmaceutical composition comprising a substantially purified HSP1 having the amino acid sequence of SEQ ID NO:1 in conjunction with a suitable pharmaceutical carrier.

The invention also provides a purified antagonist which decreases the activity of a polypeptide of SEQ ID NO:1. In one aspect the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention also provides a method for treating or preventing cancer comprising administering to a subject in need of such treatment an effective amount of a pharmaceutical composition comprising an antagonist to HSPJ1.

The invention also provides a method for treating or preventing inflammatory and immune disorders comprising administering to a subject in need of such treatment an effective amount of a pharmaceutical composition comprising an antagonist to HSPJ1.

The invention also provides a method for treating or preventing tissue damage comprising administering to a subject in need of such treatment an effective amount of a pharmaceutical composition comprising purified HSPJ1.

The invention also provides a method for detecting a polynucleotide which encodes HSPJ1 in a biological sample comprising the steps of: a) hybridizing a polynucleotide sequence complementary to HSPJ1 (SEQ ID NO:1) to nucleic acid material of a biological sample, thereby forming a hybridization complex; and b) detecting the hybridization complex, wherein the presence of the complex correlates with the presence of a polynucleotide encoding HSPJ1 in the biological sample. In a preferred embodiment, prior to hybridization, the nucleic acid material of the biological sample is amplified by the polymerase chain reaction.

The invention further provides an isolated and substantially purified polynucleotide sequence encoding the polypeptide comprising the amino acid sequence of SEQ ID NO:3 or fragments thereof and a composition comprising said polynucleotide sequence. The invention also provides a polynucleotide sequence which hybridizes under stringent conditions to the polynucleotide sequence encoding the amino acid sequence SEQ ID NO:3, or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO.4 or variants thereof. In addition, the invention provides a polynucleotide sequence which hybridizes under stringent conditions to the polynucleotide sequence of SEQ ID NO:4.

In another aspect the invention provides a composition comprising an isolated and purified polynucleotide sequence comprising the complement of SEQ ID NO:4, or fragments or variants thereof. The invention also provides a polynucleotide sequence comprising the complement of SEQ ID NO:4.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3 or a fragment thereof, the method comprising the steps of: a) culturing the host cell containing an expression vector containing at least a fragment of the polynucleotide sequence encoding HSPJ2 under conditions suitable for the expression of the polypeptide; and b) recovering the polypeptide from the host cell culture.

The invention also provides a pharmaceutical composition comprising a substantially purified HSPJ2 having the amino acid sequence of SEQ ID NO:3 in conjunction with a suitable pharmaceutical carrier.

The invention also provides a purified antagonist which decreases the activity of a polypeptide of SEQ ID NO:3. In one aspect the invention provides a purified antibody which binds to a polypeptide comprising at least a fragment of the amino acid sequence of SEQ ID NO:3.

Still further, the invention provides a purified agonist which modulates the activity of the polypeptide of SEQ ID NO:3.

The invention also provides a method for treating or preventing cancer comprising administering to a subject in need of such treatment an effective amount of a pharmaceutical composition comprising an antagonist to HSPJ2.

The invention also provides a method for treating or preventing inflammatory and immune disorders comprising administering to a subject in need of such treatment an effective amount of a pharmaceutical composition comprising an antagonist to HSPJ2.

The invention also provides a method for treating or preventing tissue damage comprising administering to a subject in need of such treatment an effective amount of a pharmaceutical composition comprising purified HSPJ2.

The invention also provides a method for detecting a polynucleotide which encodes HSPJ2 in a biological sample comprising the steps of: a) hybridizing a polynucleotide sequence complementary to HSPJ2 (SEQ ID NO:3) to nucleic acid material of a biological sample, thereby forming a hybridization complex; and b) detecting the hybridization complex, wherein the presence of the complex correlates with the presence of a polynucleotide encoding HSPJ2 in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of HSPJ1. The alignment was produced using MACDNASIS PRO™ software (Hitachi Software Engineering Co. Ltd. San Bruno, Calif.).

FIGS. 2A and 2B show the amino acid sequence alignment between HSPJ1 (SEQ ID NO:1) and DNAJ-2 (GI 306714; SEQ ID NO:5), produced using the multisequence alignment program of DNASTAR™ software (DNASTAR Inc, Madison, Wis.).

FIGS. 3A, 3B, 3C, and 3D show the amino acid sequence (SEQ ID NO:3) and nucleic acid sequence (SEQ ID NO:4)

of HSPJ2. The alignment was produced using MACDNA-SIS PRO™ software (Hitachi Software Engineering Co. Ltd. San Bruno, Calif.).

Figure 4A:
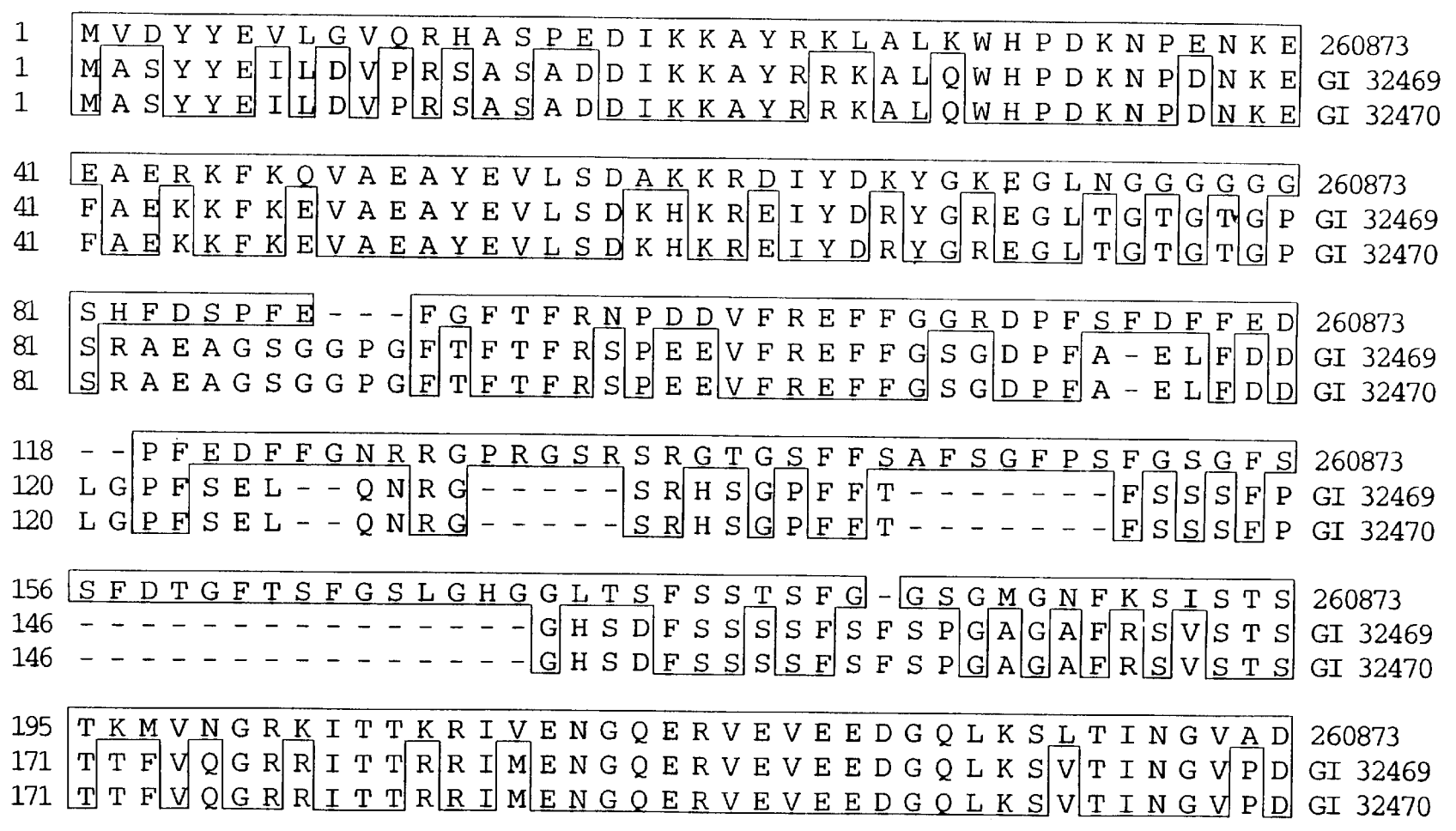

FIGS. 4A and 4B show the amino acid sequence alignments among HSPJ2 (SEQ ID NO:3), HSJ1a (GI 32469; SEQ ID NO:6) and HSJ1b (GI 32470; SEQ ID NO:7), produced using the multisequence alignment program of DNASTAR™ software (DNASTAR Inc, Madison, Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HSPJ, as used herein, refers to the amino acid sequences of substantially purified HSPJ obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HSPJ, increases or prolongs the duration of the effect of HSPJ. Agonists may include proteins, nucleic acids, carbohydrates, or any other molecules which bind to and modulate the effect of HSPJ.

An "allele" or "allelic sequence", as used herein, is an alternative form of the gene encoding HSPJ. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HSPJ as used herein include those with deletions, insertions, or substitutions of different nucleotides resulting in a polynucleotide that encodes the same or a functionally equivalent HSPJ. Included within this definition are polymorphisms which may or may not be readily detectable using a particular oligonucleotide probe of the polynucleotide encoding HSPJ, and improper or unexpected hybridization to alleles, with a locus other than the normal chromosomal locus for the polynucleotide sequence encoding HSPJ. The encoded protein may also be "altered" and contain deletions, insertions, or substitutions of amino acid residues which produce a silent change and result in a functionally equivalent HSPJ. Deliberate amino acid substitutions may be made on the basis of similarity in polarity, charge, solubility, hydrophobicity, hydrophilicity, and/or the amphipathic nature of the residues as long as the biological or immunological activity of HSPJ is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HSPJ are preferably about 5 to about 15 amino acids in length and retain the biological activity or the immunological activity of HSPJ. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to HSPJ, decreases the amount or the duration of the effect of the biological or immunological activity of HSPJ. Antagonists may include proteins, nucleic acids, carbohydrates, or any other molecules which decrease the effect of HSPJ.

As used herein, the term "antibody" refers to intact molecules as well as fragments thereof, such as Fa, F(ab')$_2$, and Fv, which are capable of binding the epitopic determinant. Antibodies that bind HSPJ polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HSPJ, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding HSPJ (SEQ ID NO:1 or SEQ ID NO:3) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, CT) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding HSPJ in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HSPJ or the encoded HSPJ. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to a high-density array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HSPJ. For example, modulation may cause an increase or a decrease in protein activity, binding characteristics, or any other biological, functional or immunological properties of HSPJ.

"Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers", "primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length HSPJ1 and fragments thereof.

The term "sample", as used herein, is used in its broadest sense. A biological sample suspected of containing nucleic acid encoding HSPJ, or fragments thereof, or HSPJ itself may comprise a bodily fluid, extract from a cell, chromosome, organelle, or membrane isolated from a cell, a cell, genomic DNA, RNA, or cDNA(in solution or bound to a solid support) a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HSPJ, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of two new human DnaJ-like proteins (hereinafter referred to as HSPJ1 and HSPJ2, and collectively, as HSPJ), the polynucleotides encoding HSPJ, and the use of these compositions for the diagnosis, prevention, or treatment of cancer and inflammatory and immune disorders.

Nucleic acids encoding the HSPJ1 of the present invention were first identified in Incyte Clone 136466 from the synovial membrane tissue cDNA library (SYNORAB01) using a computer search for amino acid sequence alignments. A consensus sequence, SEQ ID NO:2, was derived from the following overlapping and/or extended nucleic acid sequences: Incyte Clones 136466 (SYNORAB01), 1450458 (PENITUT01), 1468130 (PANCTUT02), 403306 (TMLR3DT01), 568426 (MMLR3DT01), 696229 (SYNORAT03), and 1255031 (LUNGFET03).

Figure 2A:
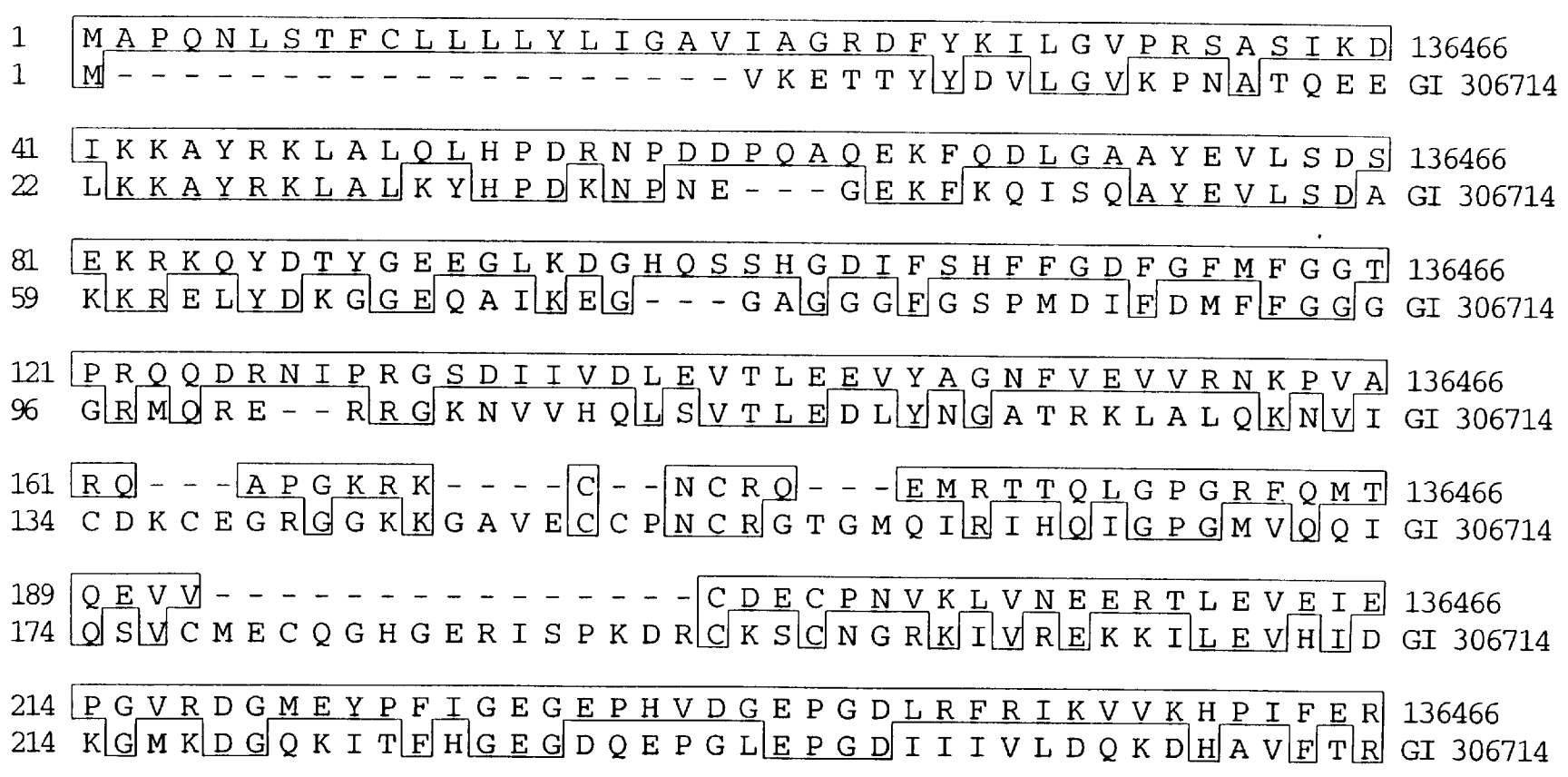

In one embodiment, the invention encompasses a polypeptide comprising the amino acid sequence of SEQ ID NO:1, as shown in FIGS. 1A through 1D. HSPJ1 is 358 amino acids in length and has a potential DnaJ domain between residues $F_{67}$ and $Y_{86}$. As shown in FIGS. 2A and 2B, HSPJ1 has chemical and structural homology with DNAJ-2 (GI 306714; SEQ ID NO:3). In particular, HSPJ1 and DNAJ-2 share 36% identity. Northern analysis shows the expression of this sequence in various libraries, at least 46% of which are immortalized or cancerous. Of particular note is the expression of HSPJ1 in disorders which involve the inflammation and immune response (18%).

Nucleic acids encoding the HSPJ2 of the present invention were first identified in Incyte Clone 260873 from the hNT2 cDNA library (HNT2RAT01) using a computer search for amino acid sequence alignments. A consensus sequence, SEQ ID NO:4, was derived from the following overlapping and/or extended nucleic acid sequences: Incyte Clones 260873, 269831 (HNT2RAT01), 264667 (HNT2AGT01), 448764 (TLYMNOT02), 1003613 10 (BRSTNOT03), 1503542 (BRAITUT07), 112064 (PITUNOT01), and 1440865 (THYRNOT03).

In another embodiment, the invention encompasses a polypeptide comprising the amino acid sequence of SEQ ID NO:3, as shown in FIGS. 3A through 3D. HSPJ2 is 330 amino acids in length and has a potential DnaJ domain between residues $F_{46}$ and $Y_{65}$. As shown in FIGS. 4A and 4B, HSPJ2 has chemical and structural homology with HSJ1a (GI 32469; SEQ ID NO:6) and HSJ1b (GI 32470; SEQ IN NO:7). In particular, HSPJ2 and HSJ1a share 46% identity, while HSPJ2 and HSJ1b share 44% identity. Northern analysis shows the expression of this sequence in various libraries, at least 59% of which are immortalized or cancerous.

The invention also encompasses HSPJ variants. A preferred HSPJ variant is one having at least 80%, and more preferably 90%, amino acid sequence identity to the HSPJ1 or HSPJ2 amino acid sequence (SEQ ID NO:1, SEQ ID NO:3). A most preferred HSPJ variant is one having at least 95% amino acid sequence identity to SEQ ID NO:1 or SEQ ID NO:3.

The invention also encompasses polynucleotides which encode HSPJ. Accordingly, any nucleic acid sequence which encodes the amino acid sequence of HSPJ can be used to produce recombinant molecules which express HSPJ. In a particular embodiment, the invention encompasses the polynucleotide comprising the nucleic acid sequence of SEQ ID NO:2 as shown in FIGS. 1A through 1D and the polynucleotide comprising the nucleic acid sequence of SEQ ID NO:4 as shown in FIG. 3A through 3D.

It will be appreciated by those skilled in the art that as a result of the degeneracy of the genetic code, a multitude of nucleotide sequences encoding HSPJ, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSPJ, and all such variations are to be considered as being specifically disclosed.

Although nucleotide sequences which encode HSPJ and its variants are preferably capable of hybridizing to the nucleotide sequence of the naturally occurring HSPJ under appropriately selected conditions of stringency, it may be advantageous to produce nucleotide sequences encoding HSPJ or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSPJ and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HSPJ and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HSPJ or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HSPJ may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSPJ may be used in recombinant DNA molecules to direct expression of HSPJ, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HSPJ.

As will be understood by those of skill in the art, it may be advantageous to produce HSPJ-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HSPJ encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HSPJ may be ligated to a heterologous sequence to encode a fusion protein. For example, to screen peptide libraries for inhibitors of HSPJ activity, it may be useful to encode a chimeric HSPJ protein that can be recognized by a commercially available antibody. A fusion protein may also be engineered to contain a cleavage site located between the HSPJ encoding sequence and the heterologous protein sequence, so that HSPJ may be cleaved and purified away from the heterologous moiety.

In another embodiment, sequences encoding HSPJ may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HSPJ, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSPJ, or any part thereof, may be altered during direct synthesis and/or combined using chemical methods with sequences from other proteins, or any part thereof, to produce a variant polypeptide.

In order to express a biologically active HSPJ, the nucleotide sequences encoding HSPJ or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HSPJ and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HSPJ. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are Ipreferable. If it is necessary to generate a cell line that contains multiple copies of the sequence encoding HSPJ, vectors based on SV40 or EBV may be used with an appropriate selectable marker.

In bacterial systems, a number of expression vectors may be selected depending upon the use intended for HSPJ. For example, when large quantities of HSPJ are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HSPJ may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HSPJ may be driven by any of a number of promoters. For example, viral promoters such as the 35S and 19S promoters of CaMV may be used alone or in combination with the omega leader sequence from TMV (Takamatsu, N. (1987) EMBO J. 6:307–31 1). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HSPJ. For example, in one such system, *Autographa californica* nuclear polyhedrosis virus (AcNPV) is used as a vector to express foreign genes in *Spodoptera frugiperda* cells or in *Trichoplusia larvae*. The sequences encoding HSPJ may be cloned into a non-essential region of the virus, such as the polyhedrin gene, and placed under control of the polyhedrin promoter. Successful insertion of HSPJ will render the polyhedrin gene inactive and produce recombinant virus lacking coat protein. The recombinant viruses may then be used to infect, for example, *S. frugiperda* cells or Trichoplusia larvae in which HSPJ may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HSPJ may be ligated into an adenovirus transcription/translation complex consisting of the late promoter and tripartite leader sequence. Insertion in a non-essential E1 or E3 region of the viral genome may be used to obtain a viable virus which is capable of expressing HSPJ in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HSPJ. Such signals include the ATG initiation codon and adjacent sequences. In cases where sequences encoding HSPJ, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HSPJ may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^{31}$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C.A. et al. (1995) Methods Mol. Biol. 55:121–131).

Although the presence/absence of marker gene expression suggests that the gene of interest is also present, its presence and expression may need to be confirmed. For example, if the sequence encoding HSPJ is inserted within a marker gene sequence, transformed cells containing sequences encoding HSPJ can be identified by the absence of marker gene function. Alternatively, a marker gene can be placed in tandem with a sequence encoding HSPJ under the control of a single promoter. Expression of the marker gene in response to induction or selection usually indicates expression of the tandem gene as well.

Alternatively, host cells which contain the nucleic acid sequence encoding HSPJ and express HSPJ may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding HSPJ can be detected by DNA—DNA or DNA-RNA hybridization or amplification using probes or fragments or fragments of polynucleotides encoding HSPJ. Nucleic acid amplification based assays involve the use of oligonucleotides or oligomers based on the sequences encoding HSPJ to detect transformants containing DNA or RNA encoding HSPJ.

A variety of protocols for detecting and measuring the expression of HSPJ, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSPJ is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSPJ include oligolabeling, nick translation, end-labeling or PCR amplification using a labeled nucleotide. Alternatively, the sequences encoding HSPJ, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HSPJ may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HSPJ may be designed to contain signal sequences which direct secretion of HSPJ through a prokaryotic or eukaryotic cell membrane. Other constructions may be used to join sequences encoding HSPJ to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSPJ may be used to facilitate purification. One such expression vector provides for expression of a fusion protein containing HSPJ and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263–281) while the enterokinase cleavage site provides a means for purifying HSPJ from the fusion protein. A discussion of vectors which contain fusion proteins is provided in Kroll, D. J. et al. (1993; DNA Cell Biol. 12:441–453).

In addition to recombinant production, fragments of HSPJ may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of ABBR may be chemically synthesized separately and combined using chemical methods to produce the full length molecule.

Therapeutics

Chemical and structural homology exits between HSPJ1 and human DNAJ-2 (GI 306714). In addition, HSPJ1 is expressed in tumors and in diseases involving inflammation and the immune system. Expression of HSPJ1 may be associated with the cascade of events that initiate and maintain inflammatory and immune responses. Therefore, HSPJ1 appears to play a role in cancer and inflammatory and immune responses. The protective effect of HSPJ1, however, may also be utilized to protect normal cells and tissues from the stress caused by pathological or cellular processes.

Therefore, in one embodiment, antagonists which decrease the activity of HSPJ1 may be administered to a subject to prevent or treat cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind HSPJ1 may be used directly as an antagonist or indirectly as a targeting or delivery mechanism for bringing a pharmaceutical agent to cells or tissue which express HSPJ1.

In another embodiment, a vector expressing the complement of the polynucleotide encoding HSPJ1 may be administered to a subject to treat or prevent cancer, and in particular, those cancers described above.

In another embodiment, antagonists which decrease the activity of HSPJ1 may be administered to a subject to prevent or treat an immune disorder. Such a disorder may include, but is not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erytematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HSPJ1 may be administered to a subject to treat or prevent an immune disorder, and in particular, the immune disorders described above.

In one embodiment, HSPJ1 or a fragment or derivative thereof may be administered to a subject to treat or prevent tissue damage. Tissue damage may result from any cause, and in particular, may be associated with disorders which include, but are not limited to, ankylosing spondylitis, heart attacks, ischemia, damage to cells such as heart muscle and nerve cells caused by ischemia, free radicals, toxins, and ultraviolet exposure, wound healing, and insulin dependent diabetes.

In another embodiment, a vector capable of expressing HSPJ1, or a fragment or a derivative thereof, may also be administered to a subject to treat tissue damage, and in particular, the tissue damage-associated disorders described above.

In still another embodiment, an agonist which modulates the activity of HSPJ1 may also be administered to a subject to treat tissue damage, and in particular, the tissue damage-associated disorders described above.

Chemical and structural homology exits among HSPJ2, human HSJ1a (GI 32469), and human HSJ1b (GI 32470). In addition, HSPJ2 is expressed in tumors and in diseases involving the inflammatory and immune system. Expression of HSPJ2 may be associated with the cascade of events that initiate and maintain inflammatory and immune responses. Therefore, HSPJ2 appears to play a role in cancer and inflammatory and immune response. The protective effect of HSPJ2, however, may also be utilized to protect normal cells and tissues from the stress caused by pathological or cellular processes.

Therefore, in one embodiment, antagonists which decrease the activity of HSPJ2 may be administered to a subject to prevent or treat cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind HSPJ2 may be used directly as an antagonist or indirectly as a targeting or delivery mechanism for bringing a pharmaceutical agent to cells or tissue which express HSPJ2.

In another embodiment, a vector expressing the complement of the polynucleotide encoding HSPJ2 may be administered to a subject to treat or prevent cancer, and in particular, the cancers described above.

In another embodiment, antagonists which decrease the activity of HSPJ2 may be administered to a subject to prevent or treat an immune disorder. Such a disorder may include, but is not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, a vector expressing the complement of the polynucleotide encoding HSPJ2 may be administered to a subject to treat or prevent an immune disorder, and in particular, the immune disorders described above.

In one embodiment, HSPJ2 or a fragment or derivative thereof may be administered to a subject to treat or prevent tissue damage. Tissue damage may result from any cause and in particular, may be associated with a disorder such as, but not limited to, ankylosing spondylitis, heart attacks, ischemia, damage to cells such as heart muscle and nerve cells caused by ischemia, free radicals, toxins, and ultraviolet exposure, wound healing, and insulin dependent diabetes.

In another embodiment, a vector capable of expressing HSPJ2, or a fragment or a derivative thereof, may also be administered to a subject to treat tissue damage, and in particular, the tissue damage-associated disorders described above.

In still another embodiment, an agonist which modulates the activity of HSPJ2 may also be administered to a subject to treat tissue damage, and in particular, the tissue damage-associated disorders described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of HSPJ may be produced using methods which are generally known in the art. In particular, purified HSPJ may be used to produce antibodies or to screen libraries of pharmaceutical agents to identify those which specifically bind HSPJ.

Antibodies to HSPJ may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSPJ or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSPJ have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HSPJ amino acids may be fused with those of another protein such as keyhole limpet hemocyanin and antibody produced against the chimeric molecule.

Monoclonal antibodies to HSPJ may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1 985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HSPJ-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HSPJ may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSPJ and its specific antibody. A two-site, monoclonal-based immunoassay utilizing monoclonal antibodies reactive to two non-interfering HSPJ epitopes is preferred, but a competitive binding assay may also be employed (Maddox, supra).

In another embodiment of the invention, the polynucleotides encoding HSPJ, or any fragment or complement thereof, may be used for therapeutic purposes. In one aspect, the complement of the polynucleotide encoding HSPJ may be used in situations in which it would be desirable to block the transcription of the mRNA. In particular, cells may be transformed with sequences complementary to polynucleotides encoding HSPJ. Thus, complementary molecules or fragments may be used to modulate HSPJ activity, or to achieve regulation of gene function. Such technology is now well known in the art, and sense or antisense oligonucleotides or larger fragments, can be designed from various locations along the coding or control regions of sequences encoding HSPJ.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HSPJ. These techniques are described both in Sambrook et al. (supra) and in Ausubel et al. (supra).

Genes encoding HSPJ can be turned off by transforming a cell or tissue with expression vectors which express high levels of a polynucleotide or fragment thereof which encodes HSPJ. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HSPJ (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSPJ.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSPJ. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, ex vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSPJ, antibodies to HSPJ, mimetics, agonists, antagonists, or inhibitors of HSPJ. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other is plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hank's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSPJ, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSPJ or fragments thereof, antibodies of HSPJ, agonists, antagonists or inhibitors of HSPJ, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSPJ may be used for the diagnosis of conditions or diseases characterized by expression of HSPJ, or in assays to monitor patients being treated with HSPJ, agonists, antagonists or inhibitors. The antibodies useful for diagnostic purposes may be prepared in the same manner as those described above for therapeutics. Diagnostic assays for HSPJ include methods which utilize the antibody and a label to detect HSPJ in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSPJ are known in the art and provide a basis for diagnosing altered or abnormal levels of HSPJ expression. Normal or standard values for HSPJ expression are established by combining body fluids or cell extracts taken from normal mammalian subjects, preferably human, with antibody to HSPJ under conditions suitable for complex formation. The amount of standard complex formation may be quantified by various methods, but preferably by photometric means. Quantities of HSPJ expressed in subject, control, and disease samples from biopsied tissues are compared with the standard values. Deviation between standard and subject values establishes the parameters for diagnosing disease.

In another embodiment of the invention, the polynucleotides encoding HSPJ may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSPJ may be correlated with disease. The diagnostic assay may be used to distinguish between absence, presence, and excess expression of HSPJ, and to monitor regulation of HSPJ levels during therapeutic intervention.

In one aspect, hybridization with PCR probes which are capable of detecting polynucleotide sequences, including genomic sequences, encoding HSPJ or closely related molecules, may be used to identify nucleic acid sequences which encode HSPJ. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSPJ, alleles, or related sequences.

Probes may also be used for the detection of related sequences, and should preferably contain at least 50% of the nucleotides from any of the HSPJ encoding sequences. The hybridization probes of the subject invention may be DNA or RNA and derived from the nucleotide sequence of SEQ ID NO:2 or from genomic sequence including promoter, enhancer elements, and introns of the naturally occurring HSPJ.

Means for producing specific hybridization probes for DNAs encoding HSPJ include the cloning of nucleic acid sequences encoding HSPJ or HSPJ derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSPJ may be used for the diagnosis of conditions, disorders, or diseases which are associated with expression of HSPJ. Examples of such conditions or diseases include cancers such as adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory and immune disorders such as AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma, ankylosing spondylitis, heart attacks, ischemia, damage to cells such as heart muscle and nerve cells caused by ischemia, free radicals, toxins, and ultraviolet exposure, wound healing, and insulin dependent diabetes. The polynucleotide sequences encoding HSPJ may be used in Southern or northern analysis, dot blot, or other membrane-based technologies; in PCR technologies; or in dipstick, pin, ELISA assays or microarrays utilizing fluids or tissues from patient biopsies to detect altered HSPJ expression. Such qualitative or quantitative methods are well known in the art.

In a particular aspect, the nucleotide sequences encoding HSPJ may be useful in assays that detect activation or induction of various cancers, particularly those mentioned above. The nucleotide sequences encoding HSPJ may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HSPJ in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSPJ, a normal or standard profile for expression is established. This may be accomplished by combining body fluids or cell extracts taken from normal subjects, either animal or human, with a sequence, or a fragment thereof, which encodes HSPJ, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSPJ may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSPJ include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of i disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devises (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HSPJ may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial PI constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, NY) may be correlated with other physical chromosome mapping techniques and genetic map data. Examples of genetic map data can be found in various scientific journals or at Online Mendelian Inheritance in Man (OMIM). Correlation between the location of the gene encoding HSPJ on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a is particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSPJ, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSPJ and the agent being tested, may be measured.

Another technique for drug screening which may be used provides for high throughput screening of compounds having suitable binding affinity to the protein of interest as described in published PCT application WO84/03564. In this method, as applied to HSPJ large numbers of different small test compounds are synthesized on a solid substrate, such as plastic pins or some other surface. The test compounds are reacted with HSPJ1 or HSPJ2, or fragments thereof, and washed. Bound HSPJ1 or HSPJ2 is then detected by methods well known in the art. Purified HSPJ1 or HSPJ2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSPJ1 or HSPJ2 specifically compete with a test compound for binding HSPJ1 or HSPJ2. In this manner, the antibodies can be used to detect the presence of any peptide which shares one or more antigenic determinants with HSPJ1 or HSPJ2.

In additional embodiments, the nucleotide sequences which encode HSPJ1 or HSPJ2 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

SYNORAB01 The cDNA library for SYNORAB01 was constructed from total RNA from rheumatoid synovial tissue, UC Davis (lot #48). The frozen tissue was ground in a mortar and pestle and lysed immediately in a buffer containing guanidinium isothiocyanate. The lysate was extracted twice with phenol chloroform at pH 8.0 and centrifuged over a CsCl cushion using a Beckman SW28 rotor in a Beckman L8-70M Ultracentrifuge (Beckman Instruments). The RNA was precipitated using 0.3 M sodium acetate and 2.5 volumes of ethanol and resuspended in water.

The RNA was prepared with the SuperScript Plasmid System for cDNA Synthesis and Plasmid Cloning (catalogue #18248-013; GIBCO/BRL, Gaithersburg Md.) with the recommended protocol. cDNAs were fractionated on a Sepharose CL4B column (catalog #275105, Pharmacia), and those cDNAs exceeding 1 kb were ligated into PSPORT1. The plasmid was transformed into chemically competent DH5a host cells (GIBCO/BRL, Gaithersburg, Md.).

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the LAMBDAZAP vector system (Stratagene); and the vector, which contains the PBLUESCRIPT phagemid (Stratagene), was transformed into cells of E. coli, strain XL1-BLUEMRF (Stratagene).

HNT2RAT01

The HNT2RAT01 cDNA library was prepared from the hNT2 cell line which exhibits characteristics of a committed neuronal precursor cell which is at an early stage of development. The hNT2 cell line can be induced by retinoic acid (RA) to differentiate, as described in Andrews PW (1984) Dev Biol 103:285–293. For purposes of this invention, hNT2 cells were induced with RA by one of two procedures. The method used in the present invention involved suspending hNT2 cells in Dulbecco's modified Eagle's medium (DMEM) including 10% fetal bovine serum and penicillin/streptomycin, treating the cells with 10 μM RA for 24 hours, and harvesting the cells immediately.

Stratagene isolated the mRNA and prepared the cDNA library. cDNAs were primed using oligo d(T) and size fractionated to isolate fragments of 500 bp and larger. Synthetic adapter oligonucleotides were ligated onto the cDNA molecules enabling them to be inserted into the UNI-ZAP vector system (Stratagene).

II Isolation and Sequencing of cDNA Clones

Plasmid DNA was purified using the Miniprep Kit (Catalogue # 77468, Advanced Genetic Technologies Corporation, Gaithersburg Md.). The recommended protocol included with the kit was employed except for the following changes. Each of the 96 wells was filled with only 1 ml of sterile Terrific Broth (Catalog # 22711, GIBCO/BRL) with carbenicillin at 25 mg/L and glycerol at 0.4%. After the wells were inoculated, the bacteria were cultured for 24 hours and lysed with 60 μl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441 f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, O or T).

The BLAST approach, as detailed in Karlin, S. and S. F. Altschul (1993; Proc Nat. Acad. Sci. 90:5893–3) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ or nucleotides and $10^{-14}$ for peptides.

Incyte nucleotide sequences were searched against the GenBapdk databases for primate (pri), rodent (rod), and mammalian sequences (mam), and deduced amino acid sequences from the same clones are searched against Gen-Bank functional protein databases, mammalian (mamp), vertebrate (vrtp) and eukaryote (eukp), for homology. The relevant database for a particular match were reported as a Glxxx±p (where xxx is pri, rod, etc and if present, p=peptide). Product score, the calculation of which is shown below, was used to determine the electronic stringency. For an exact match, product score was set at 70 with a conservative lower limit set at approximately 40 (1–2% error due to uncalled bases).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as Gen-Bank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSPJ1 or HSPJ2 occurs. Abundance and percent abundance are also reported. Abundance directly reflects the number of times a particular transcript is represented in a cDNA library, and percent abundance is abundance divided by the total number of sequences examined in the cDNA library.

V Extension of HSPJ Encoding Polynucleotides

The nucleic acid sequences of Incyte Clone 136466 or Incyte Clone 260873 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
| --- | --- |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 1 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2x Carb. The following day, several colonies were randomly picked from each plate and cultured in 150 μl of liquid LB/2x Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well.

Amplification was performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 and SEQ ID NO:4 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1 × saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J.D. et al., PCT/WO95/25 116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HSPJ1 or HSPJ2-encoding sequence, or any part thereof, is used to decrease or inhibit expression of naturally occurring HSPJ1 or HSPJ2. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HSPJ1 or HSPJ2, SEQ ID NO:1 or SEQ ID NO:3. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSPJ1 or HSPJ2-encoding transcript.

IX Expression of HSPJ

Expression of HSPJ1 or HSPJ2 is accomplished by subcloning the cDNAs into appropriate vectors and transforming the vectors into host cells. In this case, the cloning vector is also used to express HSPJ1 or HSPJ2 in E. coli. Upstream of the cloning site, this vector contains a promoter for B3-galactosidase, followed by sequence containing the amino-terminal Met, and the subsequent seven residues of B3-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of HSPJ1 or HSPJ2 into the bacterial growth media which can be used directly in the following assay for activity.

X Demonstration of HSPJ Activity

HSPJ1 or HSPJ2 induction by heat or toxins may be a demonstrated using primary cultures of human fibroblasts or human cell lines such as CCL-13, HEK293, or HEP G2 (ATCC). To heat induce HSPJ1 or HSPJ2 expression, aliquots of cells are incubated at 42° C. for 15, 30, or 60 minutes, control aliquots are incubated at 37° C. for the same time periods. To induce HSPJ1 or HSPJ2 expression by toxins, aliquots of cells are treated with 100 $\mu$M arsenite or 20 mM azetidine-2-carboxylic acid for 0, 3, 6, or 12 hours. After exposure to heat, arsinate, or the amino acid analogue, samples of the treated cells are harvested and cell lysates prepared for analysis by Western blot.

Cells are lysed in lysis buffer containing 1% Nonidet P-40, 0.15 M NaCl, 50 mM Tris-HCl, 5 mM EDTA, 2 mM N-ethylmaleimide, 2 mM phenylmethylsulfonyl fluoride, 1 mg/ml leupeptin, and 1 mg/ml pepstatin. Twenty micrograms of the cell lysate is separated on an 8% SDS- PAGE gel and transferred to a nitrocellulose membrane. After blocking with 5% nonfat dry milk/phosphate-buffered saline for 1 h, the membrane is incubated overnight at 4° C. or at room temperature for 2–4 hours with a 1:1000 dilution of anti-HSPJ1 or HSPJ2 serum in 2% nonfat dry milk/phosphate-buffered saline. The membrane is then washed and lo incubated with a 1:1000 dilution of horseradish peroxidase-conjugated goat anti-rabbit IgG (Cappel) in 2% dry milk/phosphate-buffered saline. After washing with 0.1% Tween 20 in phosphate-buffered saline, the HSPJ1 or HSPJ2 protein is detected and compared to controls by using the ECL system (Amersham).

XI Production of HSPJ Specific Antibodies

HSPJ1 or HSPJ2 that is substantially purified using PAGE electrophoresis (Sambrook, supra), or other purification techniques, is used to immunize rabbits and to produce antibodies using standard protocols. The amino acid sequence deduced from SEQ ID NO:2 or SEQ ID NO:4 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 43 1A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HSPJ Using Specific Antibodies

Naturally occurring or recombinant HSPJ1 or HSPJ2 is substantially purified by immunoaffinity chromatography using antibodies specific for HSPJ1 or HSPJ2. An immunoaffinity column is constructed by covalently coupling HSPJ1 or HSPJ2 antibody to an activated chromatographic resin, such as CNBr-activated Sepharose (Pharmacia & Upjohn). After the coupling, the resin is blocked and washed according to the manufacturer's instructions.

Media containing HSPJ1 or HSPJ2 is passed over the immunoaffinity column, and the column is washed under conditions that allow the preferential absorbance of HSPJ 1 or HSPJ2 (e.g., high ionic strength buffers in the presence of detergent). The column is eluted under conditions that disrupt antibody/HSPJ1 or HSPJ2 binding (e.g., a buffer of pH 2–3 or a high concentration of a chaotrope, such as urea or thiocyanate ion), and HSPJ 1 or HSPJ2 is collected.

XIII Identification of Molecules Which Interact with HSPJ

HSPJ1 or HSPJ2 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HSPJ1 or HSPJ2, washed and any wells with labeled HSPJ1 or HSPJ2 complex are assayed. Data obtained using different concentrations of HSPJ1 or HSPJ2 are used to calculate values for the number, affinity, and association of HSPJ1 or HSPJ2 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified human DnaJ-like-protein having a sequence selected from the group consisting of SEQ ID NO:1 and SEQ ID NO:3.

2. A pharmaceutical composition comprising a substantially purified human DnaJ-like protein of claim 1 in conjunction with a suitable pharmaceutical carrier.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 358 amino acids
        (B) TYPE: amino acid
        (C) STRANDEDNESS: single
        (D) TOPOLOGY: linear (vii) IMMEDIATE SOURCE:
        (A) LIBRARY: SYN0RAB01
        (B) CLONE: 136466

(xi) SEQUENCE DESCRIPTION: SEQ ID NO:1:

Met Ala Pro Gln Asn Leu Ser Thr Phe Cys Leu Leu Leu Leu Tyr Leu
1               5                   10                15

Ile Gly Ala Val Ile Ala Gly Arg Asp Phe Tyr Lys Ile Leu Gly Val
             20                   25                  30

Pro Arg Ser Ala Ser Ile Lys Asp Ile Lys Lys Ala Tyr Arg Lys Leu

```
                35                  40                  45
Ala Leu Gln Leu His Pro Asp Arg Asn Pro Asp Asp Pro Gln Ala Gln
                50                  55                  60

Glu Lys Phe Gln Asp Leu Gly Ala Ala Tyr Glu Val Leu Ser Asp Ser
 65                  70                  75                  80

Glu Lys Arg Lys Gln Tyr Asp Thr Tyr Gly Glu Glu Gly Leu Lys Asp
                 85                  90                  95

Gly His Gln Ser Ser His Gly Asp Ile Phe Ser His Phe Phe Gly Asp
                100                 105                 110

Phe Gly Phe Met Phe Gly Gly Thr Pro Arg Gln Gln Asp Arg Asn Ile
                115                 120                 125

Pro Arg Gly Ser Asp Ile Ile Val Asp Leu Glu Val Thr Leu Glu Glu
130                 135                 140

Val Tyr Ala Gly Asn Phe Val Glu Val Val Arg Asn Lys Pro Val Ala
145                 150                 155                 160

Arg Gln Ala Pro Gly Lys Arg Lys Cys Asn Cys Arg Gln Glu Met Arg
                165                 170                 175

Thr Thr Gln Leu Gly Pro Gly Arg Phe Gln Met Thr Gln Glu Val Val
                180                 185                 190

Cys Asp Glu Cys Pro Asn Val Lys Leu Val Asn Glu Glu Arg Thr Leu
                195                 200                 205

Glu Val Glu Ile Glu Pro Gly Val Arg Asp Gly Met Glu Tyr Pro Phe
210                 215                 220

Ile Gly Glu Gly Glu Pro His Val Asp Gly Glu Pro Gly Asp Leu Arg
225                 230                 235                 240

Phe Arg Ile Lys Val Val Lys His Pro Ile Phe Glu Arg Arg Gly Asp
                245                 250                 255

Asp Leu Tyr Thr Asn Val Thr Val Ser Leu Val Glu Ser Leu Val Gly
                260                 265                 270

Phe Glu Met Asp Ile Thr His Leu Asp Gly His Lys Val His Ile Ser
                275                 280                 285

Arg Asp Lys Ile Thr Arg Pro Gly Ala Xaa Xaa Trp Lys Lys Gly Glu
                290                 295                 300

Gly Leu Pro Asn Phe Asp Asn Asn Ile Lys Gly Ser Leu Ile Ile
305                 310                 315                 320

Thr Phe Asp Val Asp Phe Pro Lys Glu Gln Leu Thr Glu Glu Ala Arg
                325                 330                 335

Glu Gly Ile Lys Gln Leu Leu Lys Gln Gly Ser Val Gln Lys Val Tyr
                340                 345                 350

Asn Gly Leu Gln Gly Tyr
                355

(2) INFORMATION FOR SEQ ID NO:2:

(i) SEQUENCE CHARACTERISTICS:
        (A) LENGTH: 1376 base pairs
        (B) TYPE: nucleic acid
        (C) STRANDEDNESS: single
        (D) TOPOLOGY: linear (vii) IMMEDIATE SOURCE:
        (A) LIBRARY: SYN0RAB01
        (B) CLONE: 136466

(xi) SEQUENCE DESCRIPTION: SEQ ID NO:2:

TCTCACCGGG ACTCGGGACT CCCGGGAAGT GGACCGGCAG AAGAGGGGGC TAGCTAGCTG      60
```

```
TCTCTGCGGA CCAGGGAGAC CCCCGCGCCC CCCCGGTGTG AGGCGGCCTC ACAGGGCCGG    120

GTGGGCTGGC GAGCCGACGC GGCGGCGGAG GAGGCTGTGA GGAGTGTGTG AACAGGACC     180

CGGGACAGAG GAACCATGGC TCCGCAGAAC CTGAGCACCT TTTGCCTGTT GCTGCTATAC    240

CTCATCGGGG CGGTGATTGC CGGACGAGAT TTCTATAAGA TCTTGGGGGT GCCTCGAAGT    300

GCCTCTATAA AGGATATTAA AAAGGCCTAT AGGAAACTAG CCCTGCAGCT TCATCCCGAC    360

CGGAACCCTG ATGATCCACA AGCCCAGGAG AAATTCCAGG ATCTGGGTGC TGCTTATGAG    420

GTTCTGTCAG ATAGTGAGAA ACGGAAACAG TACGATACTT ATGGTGAAGA AGGATTAAAA    480

GATGGTCATC AGAGCTCCCA TGGAGACATT TTTTCACACT TCTTTGGGGA TTTTGGTTTC    540

ATGTTTGGAG GAACCCCTCG TCAGCAAGAC AGAAATATTC AAGAGGAAG TGATATTATT     600

GTAGATCTAG AAGTCACTTT GGAAGAAGTA TATGCAGGAA ATTTTGTGGA AGTAGTTAGA    660

AACAAACCTG TGGCAAGGCA GGCTCCTGGC AAACGGAAGT GCAATTGTCG GCAAGAGATG    720

CGGACCACCC AGCTGGGCCC TGGGCGCTTC CAAATGACCC AGGAGGTGGT CTGCGACGAA    780

TGCCCTAATG TCAAACTAGT GAATGAAGAA CGAACGCTGG AAGTAGAAAT AGAGCCTGGG    840

GTGAGAGACG GCATGGAGTA CCCCTTTATT GGAGAAGGTG AGCCTCACGT GGATGGGGAG    900

CCTGGAGATT TACGGTTCCG AATCAAAGTT GTCAAGCACC CAATATTTGA AAGGAGAGGA    960

GATGATTTGT ACACAAATGT GACAGTCTCA TTAGTTGAGT CACTGGTTGG CTTTGAGATG   1020

GATATTACTC ACTTGGATGG TCACAAGGTA CATATTTCCC GGGATAAGAT CACCAGGCCA   1080

GGAGCGAANT ANTGGAAGAA AGGGGAAGGG CTCCCCAACT TTGACAACAA CAATATCAAG   1140

GGCTCTTTGA TAATCACTTT TGATGTGGAT TTTCCAAAAG AACAGTTAAC AGAGGAAGCG   1200

AGAGAAGGTA TCAAACAGCT ACTGAAACAA GGGTCAGTGC AGAAGGTATA CAATGGACTG   1260

CAAGGATATT GAGAGTGAAT AAAATTGGAC TTTGTTTAAA ATAAGTGAAT AAGCGATATT   1320

TATTATCTGC AAGGTTTTTT TGTGTGTGTT TTTGTTTTTA TTTTCAATAT GCAAGT       1376
```

(2) INFORMATION FOR SEQ ID NO:3:

(i) SEQUENCE CHARACTERISTICS:
        (A) LENGTH: 330 amino acids
        (B) TYPE: amino acid
        (C) STRANDEDNESS: single
        (D) TOPOLOGY: linear (vii) IMMEDIATE SOURCE:
        (A) LIBRARY: HNT2RAT01
        (B) CLONE: 260873

(xi) SEQUENCE DESCRIPTION: SEQ ID NO:3:

```
Met Val Asp Tyr Tyr Glu Val Leu Gly Val Gln Arg His Ala Ser Pro
 1               5                  10                  15

Glu Asp Ile Lys Lys Ala Tyr Arg Lys Leu Ala Leu Lys Trp His Pro
            20                  25                  30

Asp Lys Asn Pro Glu Asn Lys Glu Glu Ala Glu Arg Lys Phe Lys Gln
        35                  40                  45

Val Ala Glu Ala Tyr Glu Val Leu Ser Asp Ala Lys Lys Arg Asp Ile
    50                  55                  60

Tyr Asp Lys Tyr Gly Lys Glu Gly Leu Asn Gly Gly Gly Gly Gly Gly
65                  70                  75                  80

Ser His Phe Asp Ser Pro Phe Glu Phe Gly Phe Thr Phe Arg Asn Pro
                85                  90                  95

Asp Asp Val Phe Arg Glu Phe Phe Gly Gly Arg Asp Pro Phe Ser Phe
           100                 105                 110
```

-continued

```
Asp Phe Phe Glu Asp Pro Phe Asp Phe Gly Asn Arg Arg Gly
        115                 120                 125
Pro Arg Gly Ser Arg Ser Arg Gly Thr Gly Ser Phe Phe Ser Ala Phe
130                 135                 140
Ser Gly Phe Pro Ser Phe Gly Ser Gly Phe Ser Phe Asp Thr Gly
145                 150                 155                 160
Phe Thr Ser Phe Gly Ser Leu Gly His Gly Gly Leu Thr Ser Phe Ser
                165                 170                 175
Ser Thr Ser Phe Gly Gly Ser Gly Met Gly Asn Phe Lys Ser Ile Ser
                180                 185                 190
Thr Ser Thr Lys Met Val Asn Gly Arg Lys Ile Thr Thr Lys Arg Ile
                195                 200                 205
Val Glu Asn Gly Gln Glu Arg Val Glu Val Glu Glu Asp Gly Gln Leu
    210                 215                 220
Lys Ser Leu Thr Ile Asn Gly Val Ala Asp Asp Ala Leu Xaa Glu
225                 230                 235                 240
Glu Arg Met Arg Arg Gly Gln Asn Val Leu Pro Ala Gln Pro Ala Gly
                245                 250                 255
Leu Arg Pro Pro Lys Pro Pro Arg Pro Ala Ser Leu Leu Arg His Xaa
                260                 265                 270
Pro His Cys Leu Ser Lys Glu Glu Gly Glu Gln Asp Arg Pro Trp Ala
            275                 280                 285
Pro Xaa Xaa Trp Xaa Pro Leu Ala Ser Xaa Ala Gly Xaa Xaa Glu Gly
        290                 295                 300
Xaa Lys Arg Met Xaa Ala Glu Ala Glu Arg Gly Val Glu Glu Glu
305                 310                 315                 320
Val Asp Gln Arg Gln Ser Leu Asp Arg Thr
                325                 330

(2) INFORMATION FOR SEQ ID NO:4:

(i) SEQUENCE CHARACTERISTICS:
        (A) LENGTH: 1330 base pairs
        (B) TYPE: nucleic acid
        (C) STRANDEDNESS: single
        (D) TOPOLOGY: linear (vii) IMMEDIATE SOURCE:
        (A) LIBRARY: HNT2RAT01
        (B) CLONE: 260873

(xi) SEQUENCE DESCRIPTION: SEQ ID NO:4:

CGNAGGAGAG NAAAGGAAAG NCGCCGCAGG AGCCGCCGCN ACCACCAGCG NCACANTCCT      60

GGNGCTNTGA GGAGATTCGG GCCGTCACCC TGCCTCCCCT GCTTCCCGCC ACCGGCCGCT     120

TCTTTCCTCG GACCCATTCC AACAATCTCG TAAAACATGG TGGATTACTA TGAAGTTCTA    180

GGCGTGCAGA GACATGCCTC ACCCGAGGAT ATTAAAAAGG CATATCGGAA ACTGGCACTG    240

AAGTGGCATC CAGATAAAAA TCCTGAGAAT AAAGAAGAAG CAGAGAGAAA ATTCAAGCAA    300

GTAGCGGAGG CATATGAAGT GCTGTCGGAT GCTAAGAAAC GGGACATCTA TGACAAATAT    360

GGCAAAGAAG GATTAAATGG TGGNGGNGGN GGTGGAAGTC ATTTTGACAG TCCATTTGAA    420

TTTGGCTTCA CATTCCGTAA CCCAGATGAT GTCTTCAGGG AATTTTTTGG TGGAAGGGAC    480

CCATTTTCAT TGACTTCTT TGAAGACCCT TTTGAGGACT TCTTTGGGAA TCGAAGGGGT    540

CCCCGAGGAA GCAGAAGCCG AGGGACGGGG TCGTTTTTCT CTGCGTTCAG TGGATTTCCG    600

TCTTTTGGAA GTGGATTTTC TTCTTTTGAT ACAGGATTTA CTTCATTTGG GTCACTAGGT    660
```

```
CACGGGGGCC TCACTTCATT CTCTTCCACG TCATTTGGTG GTAGTGGCAT GGGCAACTTC      720

AAATCGATAT CAACTTCAAC TAAAATGGTT AATGGCAGAA AAATCACTAC AAAGAGAATT      780

GTCGAGAACG GTCAAGAAAG AGTAGAAGTT GAAGAAGATG GCCAGTTAAA GTCCTTAACA      840

ATAAATGGTG TKGCCGACGA CGATGCCCTC GSTGAGGAGC GCATGCGGAG AGGCCAGAAC      900

GTCCTGCCAG CCCAGCCTGC CGGCCTCCGA CCGCCGAAGC CGCCCCGGCC TGCCTCGTTG      960

CTGAGACACG NGCCTCATTG TCTCTCTAAG GAGGAGGGCG AGCAGGACCG ACCTTGGGCA     1020

CCCGNGNCCT GGNNCCCCCT CGCTTCCNCA GCAGGNTTNN AAGAAGGTNG CAAGAGGATG     1080

NAAGCAGAAG CAGAGAGAGG AGTCGAAGAA GAAGAAGTCG ACCAAAGGCA ATCACTAGAC     1140

CGGACTTGAG GCACGCGGTG CACCCCCAGA CGCTGGCGCT CCACCGTGCT CGGCATGCGG     1200

TCGTGCACAC GCGCTAGGTA GCAGCGTCGG TCAGGACTGT CTCGAGGCCA CACTCGCTCG     1260

GCAGGATTAT GCGATCACGG ATCAGTCAGA GCAGGGTCAG GAGACGGGGC TGACGGCACG     1320

GGTGGCGGGG                                                          1330
```

(2) INFORMATION FOR SEQ ID NO:5:

(i) SEQUENCE CHARACTERISTICS:
        (A) LENGTH: 397 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 306714

(xi) SEQUENCE DESCRIPTION: SEQ ID NO:5:

```
Met Val Lys Glu Thr Thr Tyr Tyr Asp Val Leu Gly Val Lys Pro Asn
 1               5                  10                  15

Ala Thr Gln Glu Glu Leu Lys Lys Ala Tyr Arg Lys Leu Ala Leu Lys
                20                  25                  30

Tyr His Pro Asp Lys Asn Pro Asn Glu Gly Glu Lys Phe Lys Gln Ile
            35                  40                  45

Ser Gln Ala Tyr Glu Val Leu Ser Asp Ala Lys Lys Arg Glu Leu Tyr
 50                  55                  60

Asp Lys Gly Gly Glu Gln Ala Ile Lys Glu Gly Gly Ala Gly Gly Gly
 65                  70                  75                  80

Phe Gly Ser Pro Met Asp Ile Phe Asp Met Phe Phe Gly Gly Gly Gly
                85                  90                  95

Arg Met Gln Arg Glu Arg Arg Gly Lys Asn Val Val His Gln Leu Ser
            100                 105                 110

Val Thr Leu Glu Asp Leu Tyr Asn Gly Ala Thr Arg Lys Leu Ala Leu
            115                 120                 125

Gln Lys Asn Val Ile Cys Asp Lys Cys Glu Gly Arg Gly Gly Lys Lys
 130                 135                 140

Gly Ala Val Glu Cys Cys Pro Asn Cys Arg Gly Thr Gly Met Gln Ile
 145                 150                 155                 160

Arg Ile His Gln Ile Gly Pro Gly Met Val Gln Gln Ile Gln Ser Val
                165                 170                 175

Cys Met Glu Cys Gln Gly His Gly Glu Arg Ile Ser Pro Lys Asp Arg
            180                 185                 190

Cys Lys Ser Cys Asn Gly Arg Lys Ile Val Arg Glu Lys Lys Ile Leu
            195                 200                 205
```

```
Glu Val His Ile Asp Lys Gly Met Lys Asp Gly Gln Lys Ile Thr Phe
    210                 215                 220

His Gly Glu Gly Asp Gln Glu Pro Gly Leu Glu Pro Gly Asp Ile Ile
225                 230                 235                 240

Ile Val Leu Asp Gln Lys Asp His Ala Val Phe Thr Arg Arg Gly Glu
            245                 250                 255

Asp Leu Phe Met Cys Met Asp Ile Gln Leu Val Glu Ala Leu Cys Gly
                260                 265                 270

Phe Gln Lys Pro Ile Ser Thr Leu Asp Asn Arg Thr Ile Val Ile Thr
            275                 280                 285

Ser His Pro Gly Gln Ile Val Lys His Gly Asp Ile Lys Cys Val Leu
    290                 295                 300

Asn Glu Gly Met Pro Ile Tyr Arg Arg Pro Tyr Glu Lys Gly Arg Leu
305                 310                 315                 320

Ile Ile Glu Phe Lys Val Asn Phe Pro Glu Asn Gly Phe Leu Ser Pro
                325                 330                 335

Asp Lys Leu Ser Leu Leu Glu Lys Leu Leu Pro Glu Arg Lys Glu Val
            340                 345                 350

Glu Glu Thr Asp Glu Met Asp Gln Val Glu Leu Val Asp Phe Asp Pro
        355                 360                 365

Asn Gln Glu Arg Arg Arg His Tyr Asn Gly Glu Ala Tyr Glu Asp Asp
    370                 375                 380

Glu His His Pro Arg Gly Gly Val Gln Cys Gln Thr Ser
385                 390                 395

(2) INFORMATION FOR SEQ ID NO:6:

(i) SEQUENCE CHARACTERISTICS:
        (A) LENGTH: 351 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 32469

(xi) SEQUENCE DESCRIPTION: SEQ ID NO:6:

Met Ala Ser Tyr Tyr Glu Ile Leu Asp Val Pro Arg Ser Ala Ser Ala
1               5                   10                  15

Asp Asp Ile Lys Lys Ala Tyr Arg Arg Lys Ala Leu Gln Trp His Pro
            20                  25                  30

Asp Lys Asn Pro Asp Asn Lys Glu Phe Ala Glu Lys Phe Lys Glu
        35                  40                  45

Val Ala Glu Ala Tyr Glu Val Leu Ser Asp Lys His Lys Arg Glu Ile
    50                  55                  60

Tyr Asp Arg Tyr Gly Arg Glu Gly Leu Thr Gly Thr Gly Thr Gly Pro
65                  70                  75                  80

Ser Arg Ala Glu Ala Gly Ser Gly Gly Pro Gly Phe Thr Phe Thr Phe
                85                  90                  95

Arg Ser Pro Glu Glu Val Phe Arg Glu Phe Phe Gly Ser Gly Asp Pro
            100                 105                 110

Phe Ala Glu Leu Phe Asp Asp Leu Gly Pro Phe Ser Glu Leu Gln Asn
        115                 120                 125

Arg Gly Ser Arg His Ser Gly Pro Phe Phe Thr Phe Ser Ser Ser Phe
    130                 135                 140

Pro Gly His Ser Asp Phe Ser Ser Ser Ser Phe Ser Phe Ser Pro Gly
```

```
                       145                 150                 155                 160
Ala Gly Ala Phe Arg Ser Val Ser Thr Ser Thr Thr Phe Val Gln Gly
                165                 170                 175

Arg Arg Ile Thr Thr Arg Arg Ile Met Glu Asn Gly Gln Glu Arg Val
                180                 185                 190

Glu Val Glu Glu Asp Gly Gln Leu Lys Ser Val Thr Ile Asn Gly Val
                195                 200                 205

Pro Asp Asp Leu Ala Arg Gly Leu Glu Leu Ser Arg Arg Glu Gln Gln
                210                 215                 220

Pro Ser Val Thr Ser Arg Ser Gly Gly Thr Gln Val Gln Thr Pro
225                 230                 235                 240

Ala Ser Cys Pro Leu Asp Ser Asp Leu Ser Glu Asp Glu Leu Gln
                245                 250                 255

Leu Ala Met Ala Tyr Ser Leu Ser Glu Met Glu Ala Ala Gly Lys Lys
                260                 265                 270

Pro Ala Gly Gly Arg Glu Ala Gln His Arg Gln Gly Arg Pro Arg
                275                 280                 285

Pro Ser Thr Lys Ile Gln Ala Trp Gly Gly Pro Arg Arg Val Arg Gly
                290                 295                 300

Val Lys Gln Pro Asn Ala Val His Pro Gln Arg Arg Arg Pro Leu Ala
305                 310                 315                 320

Ala Ser Ser Ser Glu His Arg Ala Gln Pro Asp Leu Ile Gln Ile Leu
                325                 330                 335

Thr Gly Gly Ser Asp Ser Leu Trp Glu Glu Lys Arg Gly Val Ser
                340                 345                 350

(2) INFORMATION FOR SEQ ID NO:7:

(i) SEQUENCE CHARACTERISTICS:
        (A) LENGTH: 277 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 32470

(xi) SEQUENCE DESCRIPTION: SEQ ID NO:7:

Met Ala Ser Tyr Tyr Glu Ile Leu Asp Val Pro Arg Ser Ala Ser Ala
1               5                   10                  15

Asp Asp Ile Lys Lys Ala Tyr Arg Arg Lys Ala Leu Gln Trp His Pro
                20                  25                  30

Asp Lys Asn Pro Asp Asn Lys Glu Phe Ala Glu Lys Lys Phe Lys Glu
                35                  40                  45

Val Ala Glu Ala Tyr Glu Val Leu Ser Asp Lys His Lys Arg Glu Ile
50                  55                  60

Tyr Asp Arg Tyr Gly Arg Glu Gly Leu Thr Gly Thr Gly Thr Gly Pro
65                  70                  75                  80

Ser Arg Ala Glu Ala Gly Ser Gly Gly Pro Gly Phe Thr Phe Thr Phe
                85                  90                  95

Arg Ser Pro Glu Glu Val Phe Arg Glu Phe Phe Gly Ser Gly Asp Pro
                100                 105                 110

Phe Ala Glu Leu Phe Asp Asp Leu Gly Pro Phe Ser Glu Leu Gln Asn
                115                 120                 125

Arg Gly Ser Arg His Ser Gly Pro Phe Phe Thr Phe Ser Ser Ser Phe
                130                 135                 140
```

-continued

```
Pro Gly His Ser Asp Phe Ser Ser Ser Phe Ser Phe Ser Pro Gly
145                 150                 155                 160

Ala Gly Ala Phe Arg Ser Val Ser Thr Ser Thr Thr Phe Val Gln Gly
            165                 170                 175

Arg Arg Ile Thr Thr Arg Arg Ile Met Glu Asn Gly Gln Glu Arg Val
            180                 185                 190

Glu Val Glu Glu Asp Gly Gln Leu Lys Ser Val Thr Ile Asn Gly Val
        195                 200                 205

Pro Asp Asp Leu Ala Arg Gly Leu Glu Leu Ser Arg Arg Glu Gln Gln
    210                 215                 220

Pro Ser Val Thr Ser Arg Ser Gly Gly Thr Gln Val Gln Gln Thr Pro
225                 230                 235                 240

Ala Ser Cys Pro Leu Asp Ser Asp Leu Ser Glu Asp Glu Asp Leu Gln
                245                 250                 255

Leu Ala Met Ala Tyr Ser Leu Ser Glu Met Glu Ala Ala Gly Lys Lys
            260                 265                 270

Pro Ala Asp Val Phe
            275
```